United States Patent
Rönnberg et al.

(12)

(10) Patent No.: US 6,471,681 B1
(45) Date of Patent: Oct. 29, 2002

(54) ABSORBENT ARTICLE

(75) Inventors: Peter Rönnberg, Mölndal (SE); Anders Gustavsson, Billdal (SE); Eva Fransson, Mölndal (SE)

(73) Assignee: SCA Hygiene Products AB, Gothenburg (DE)

( * ) Notice: Subject to any disclaimer, the term of this patent is extended or adjusted under 35 U.S.C. 154(b) by 0 days.

(21) Appl. No.: 09/380,308
(22) PCT Filed: Feb. 11, 1998
(86) PCT No.: PCT/SE98/00232
§ 371 (c)(1),
(2), (4) Date: Oct. 27, 1999
(87) PCT Pub. No.: WO98/37838
PCT Pub. Date: Sep. 3, 1998

(30) Foreign Application Priority Data

Feb. 28, 1997 (SE) ................................................ 9700733

(51) Int. Cl.⁷ ................................................ A61F 13/15
(52) U.S. Cl. ............................ 604/385.19; 604/385.27; 604/385.28
(58) Field of Search ................... 604/385.01, 385.08, 604/385.21, 385.23, 385.24, 385.26, 385.25–385.28, 386, 389, 391, 392, 385.19

(56) References Cited

U.S. PATENT DOCUMENTS

| | | | |
|---|---|---|---|
| 5,137,526 A | * | 8/1992 | Coates ........................ 604/391 |
| 5,454,803 A | * | 10/1995 | Sageser et al. .......... 604/385.2 |
| 5,620,431 A | | 4/1997 | LeMahieu et al. |
| 5,931,825 A | * | 8/1999 | Kuen et al. ............... 604/385.2 |
| 6,152,907 A | * | 11/2000 | Widlund et al. ........ 604/385.08 |
| 6,168,583 B1 | * | 1/2001 | Tanji et al. .................. 210/330 |
| 6,328,724 B1 | * | 12/2001 | Ronnberg et al. ....... 604/385.01 |

FOREIGN PATENT DOCUMENTS

| | | |
|---|---|---|
| EP | 0 486 006 | 5/1992 |
| WO | WO 94/18927 | 9/1994 |
| WO | WO 97/30671 | 8/1997 |

* cited by examiner

*Primary Examiner*—Dennis Ruhl
*Assistant Examiner*—Jamisue Webb
(74) *Attorney, Agent, or Firm*—Young & Thompson

(57) ABSTRACT

An absorbent article with a liquid barrier layer which lies nearest the user's body and which includes a first and a second pair of elastic members. The surface layer is used as the article's supporting unit in which other included parts, such as reverse layer and absorption body, are suspended. The surface layer also has an elongate opening which permits liquid communication from the user's genitals to the inside of the article.

8 Claims, 2 Drawing Sheets

ABSORBENT ARTICLE

CROSS REFERENCE TO RELATED APPLICATION

This is the 35 USC 371 national stage of International application PCT/SE98/00232 filed on Feb. 11, 1998, which designated the United States of America.

TECHNICAL FIELD

The present invention relates to a liquid-absorbing article, intended for single use.

BACKGROUND

Liquid-absorbing articles, for example diapers, provided with elastic for giving the article a certain desired shape in the position of use, have previously been disclosed. With articles such as diapers and incontinence protectors which are intended to surround the lower part of the user's trunk in the manner of pants, the main object of the elastic is to create an elevated elastic edge fitting tightly round the wearer's legs, in order by this means to keep bodily fluid inside the article. This type of elastic is usually called leg elastic.

On many articles there is. also another type of elastic whose purpose is to create raised barriers which are intended to prevent a free flow of liquid in the article, since such uncontrolled flow of liquid can lead to liquid reaching the edge areas of the article and leaking out of the article. Raised elastic barriers can be used alone or can be combined with leg elastic. The raised barriers are especially effective when the wearer is lying on his/her side, or when the flows of liquid are substantial or sudden. Arranging raised barriers in an absorbent article also prevents spread of faeces in the article.

It is already known, for example from European Patent 0,391,476, to provide a diaper with raised barriers. These barriers are folded down towards the absorption body at their respective mid-crotch sections, and secured in this position by means of adhesive. This provides raised barriers which have a lower height above the absorption body at mid-crotch than at the respective front and rear portions of the diaper, which is said to give increased comfort to a person using the diaper. It is further stated that the raised barriers have the main purpose of forming a dam, while the actual seal against leakage of liquid is made up of leg elastic.

U.S. Pat. No. 5,413,570 also discloses a method of obtaining raised liquid barriers. The liquid barriers are secured on top of the surface material of the diaper and have an edge portion which is secured on the diaper and an edge portion which is free. The secured edge portions of the barriers can in this case be straight, while the opposite free edge portion is curved and provided with elastic. Alternatively, the barriers can consist of strips of elastic of uniform width. The strips are in this case arranged on the diaper with a curvature which converges towards mid-crotch, or alternatively diverges from the latter.

European Patent 0,374,640 discloses another method of creating raised barriers of varying height. The front end portions of the originally straight barriers are folded towards the centre of the diaper and are secured, while, conversely, the rear end portions of the barriers are folded in the direction towards the rear corner portions of the diaper and secured. Thus, each barrier comes to be folded towards the centre of the diaper at its front edge and folded out from the centre at its rear edge.

WO 94/18927 discloses a pant diaper having elastic side panels and longitudinally extending elastic barriers.

TECHNICAL PROBLEM

A problem which arises when using absorbent articles of the abovementioned type is that of obtaining cooperation between different elastic members in order thereby to obtain a fully satisfactory sealing effect without compromising the comfort for the wearer. Another problem is that absorbent articles are compressed between the user's legs during use. In the case of absorbent articles having leakage barriers in the form of liquid-obstructing strips of material, or flaps containing essentially liquid-impermeable material, there is a considerable risk that the barrier material will spread across the liquid-permeable cover layer of the article and completely or partially block the passage of liquid into the article's absorption body.

BRIEF DESCRIPTION OF THE INVENTION

The object of the present invention is to make available an absorbent article, such as a diaper or an incontinence protector, with a preferably elongate absorption body, consisting of one or more layers of absorbent material. The article furthermore comprises a liquid barrier layer which, during use, is intended to be directed towards the user, and a liquid-impermeable backing layer which, during use, is directed away from the user, and a liquid-permeable surface layer. placed between the liquid-impermeable backing layer and the liquid barrier layer. The absorption body is hereby enclosed between said backing layer and said liquid-permeable surface layer. The article furthermore includes a first pair of elastic members whose main direction of extension coincides with the longitudinal direction of the article, and a second pair of elastic members whose main direction of extension coincides with the longitudinal direction of the article, the two said pairs of elastic members being secured to the liquid barrier layer. This liquid-impermeable surface layer is connected in a liquid-tight manner to the backing layer within an edge portion which is formed by these layers and runs around the article, the liquid barrier layer having an elongate opening which permits an unimpeded communication of bodily excretions between the user's genitals and the liquid-permeable surface layer.

The characterizing feature of the invention is that the outer liquid-impermeable backing layer is essentially nonelastic, while the liquid barrier layer comprises both the first pair of elastic members and the second pair of elastic members. As a result of this, said liquid barrier layer alone constitutes the supporting portions of the article during use, as well as the portions bearing against the user's body, the liquid barrier layer having portions which are designed to directly or indirectly carry means for securing the article on a user. Such securing means can be, for example, tape, hook-and-loop surfaces, snap fasteners, buttons and button holes, hooks, eyelets or the like. The securing means can be attached directly to the liquid barrier layer or can be attached to a piece of material which is in turn attached to the liquid barrier layer. According to a particularly advantageous embodiment, the securing means are secured on the end portions of a belt, which is in turn secured to the liquid barrier layer. Such a securing belt can either be connected permanently to the liquid barrier layer or can be removable. One advantage of a removable securing belt is that it provides the possibility of re-using the belt.

The liquid barrier layer is thus intended, during use of the article, to be kept in contact against the user's body as a result of the action of the elastic members. By arranging the elastic members in the outer liquid barrier surface layer directed towards the user, the elastic members form the liquid barrier layer in such a way that the latter is given a fit which is, from the point of view of leakage, particularly favourable for user comfort. The shape and function of the absorption body is in this case affected to only a slight extent by the contracting forces from the elastic members. In this way, the risk of deformation of the absorption body is considerably reduced. For example, the risk of undesired creases, cracks or the like occurring in the absorption body is minimized.

BRIEF DESCRIPTION OF THE FIGURES

The invention will be described in greater detail below, with reference being made to the figures in the attached drawings, where.

DETAILED DESCRIPTION OF ILLUSTRATIVE EMBODIMENT

Figure 1:
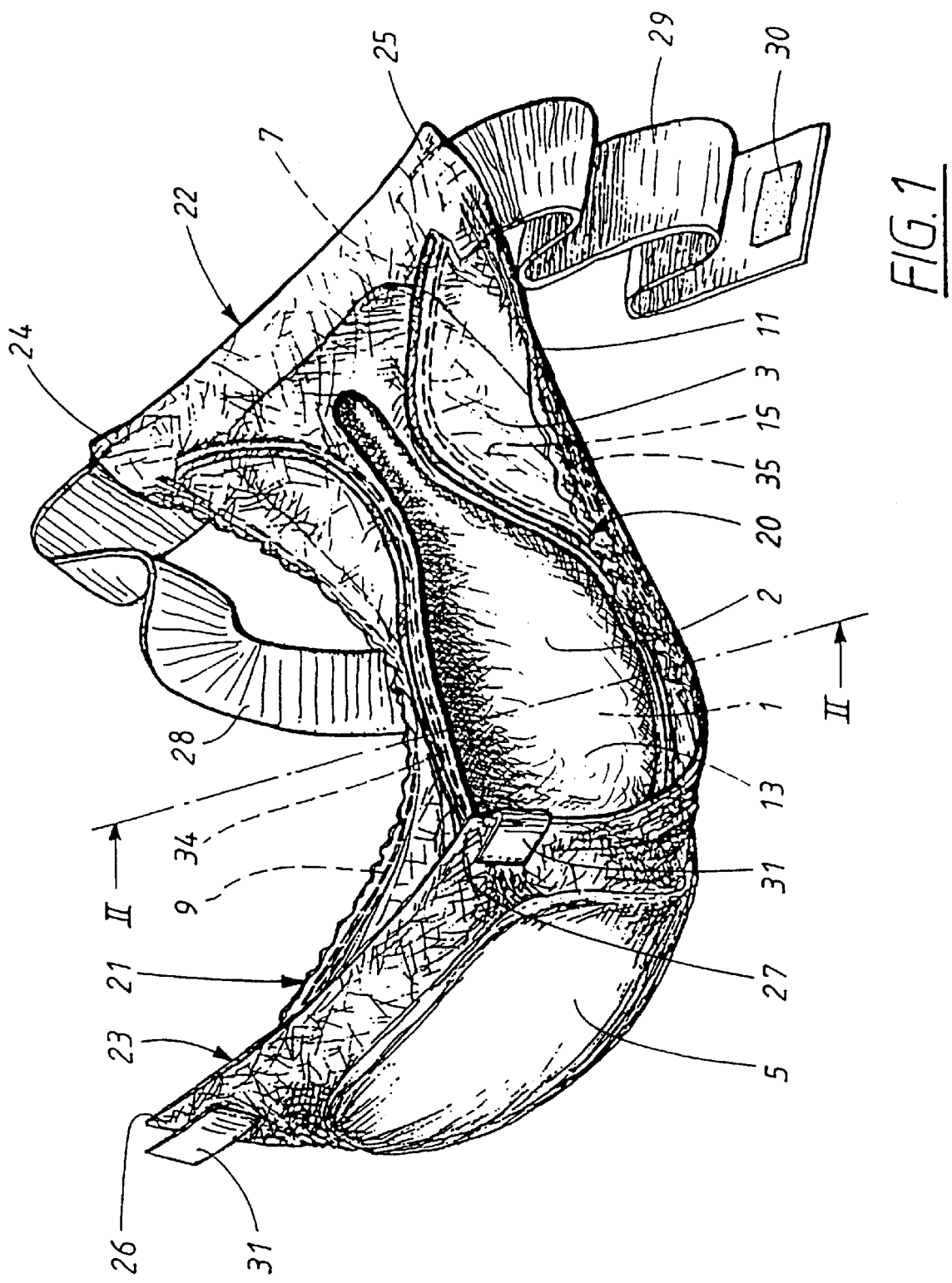
FIG. 1 shows a perspective view of an incontinence protector according to the invention, viewed from that side which, during use, is intended to be directed towards the user.

FIG. 1 shows an incontinence protector with an elongate absorption body 1. The absorption body 1 can be of any type suitable for the purpose. For example, the absorption body 1 can be made up of one or more layers of absorbent fibres such as cellulose fluff pulp, rayon, cotton or the like, and tissue material, nonwoven material, foam or other absorbent or nonabsorbent components.

In order to increase the absorption capacity, the absorption body 1 can contain so-called superabsorbents, which are polymer materials, usually present in the form of particles, flakes, fibres, or the like, and with the ability to absorb several times their own weight of bodily fluid and form an aqueous gel. Superabsorbents can be present as one or more layers or areas in the absorption body 1 or can be mixed with other absorption materials, such as cellulose fluff pulp or absorbent fibre wadding of another type. Moreover, the superabsorbents can of course be arranged in a nonabsorbent supporting structure, for example a fibre layer of nonabsorbent fibres.

The incontinence protector also has a liquid barrier layer 3 which, during use, is intended to be directed towards the user, a liquid-impermeable backing layer 5 which is directed away from the user during use, and a liquid-permeable surface layer 2 placed between the liquid-impermeable backing layer 5 and the liquid barrier layer 3. The absorption body 1 is in this case enclosed between said backing layer 5 and the said liquid-permeable surface layer 2.

The liquid-permeable surface layer 2 expediently consists of a soft, flexible material such as so-called nonwoven material, perforated plastic film, a net of plastic or textile, or the like. The surface layer 2 should have a high admittance capacity so as to be able to let the excreted bodily fluid pass quickly into the absorption body 1 lying within.

The liquid-tight reverse layer 5 is generally some type of liquid-obstructing material, or material laminate, and most often comprises a thin, liquid-impermeable plastic film. However, it is also possible to use hydrophobic, liquid-impermeable nonwoven materials, hydrophobicized nonwoven material, laminates of different types of nonwoven material, for example comprising a layer of so-called meltblown material, or the like.

The liquid barrier layer 3 arranged over the liquid-permeable surface layer 2 can consist, for example, of a liquid-impermeable material of any one of the types mentioned in connection with the backing layer 5. It is not necessary for the liquid barrier layer 3 to be completely liquid-impermeable; instead, for many applications it may be sufficient for the liquid barrier layer 3 to resist liquid penetration, at least for a period of time corresponding to the time it takes for the bodily fluid to pass in through the liquid-permeable surface layer 2 and be absorbed by the absorption body.

A first pair of elastic members 7 and a second pair of elastic members 9 are secured to the liquid barrier layer 3, for example by adhesive-bonding, or welding. The elastic members 7, 9 can consist, for example, of one or more elastic filaments, elastic bands, nets, nonwoven strips, foam strips, or the like. Different types of elastic laminates can also be used. Although the incontinence protector shown in FIG. 1 is provided with special elastic members 7, 9, it is of course possible instead to imagine these being completely or partially omitted by means of using a liquid barrier layer which is elastic in itself, or which at least has elastic portions which provide the desired elastic effect in the longitudinal direction of the incontinence protector.

The liquid barrier layer 3 is in turn. connected in a liquid-impermeable manner to the reverse layer 5 within an edge portion 11 formed by these two layers and running around the incontinence protector. The liquid barrier layer 3 furthermore has an elongate opening 13 which is arranged centrally on the layer and which permits an unimpeded flow of bodily excretions from the user's genitals to the liquid-permeable surface layer 2 and the absorption body 1 lying within.

The outer liquid-impermeable backing layer 5 of the incontinence protector is essentially nonelastic, while the elastic members 7, 9 included in the incontinence protector are arranged in the liquid barrier layer 3. In this way, the liquid barrier layer 3 alone constitutes the supporting portions of the incontinence protector during use. Moreover, portions of the liquid barrier layer 3, by being contracted and raised by the elastic members 7, 9, come to bear sealingly against the user's body during use. Although the incontinence protector shown has been described with only leg elastic 9 and elastic, raised barriers 7 running in the longitudinal direction of the incontinence protector, further elastic members can of course be used within the context of the invention. For example, the incontinence protector can be provided with waist elastic, or with elastic members arranged to form the absorption body of the incontinence protector. However, in order to minimize the risk of the absorption body being affected in an undesired way by elastic members whose degree of extension changes during use as a result of the movements of the user's body, all such elastic members should be arranged in the liquid barrier layer 3.

As has already been mentioned, the incontinence protector has an essentially elongate shape with two longitudinal side edges 20, 21 and two transverse end edges 22, 23.

The liquid barrier layer 3 also has portions which are designed to carry means for securing the incontinence protector on a user. These portions are found, in the illustrative embodiment shown, at corner portions 24–27 of the incontinence protector, where the side edges 20, 21 and the end edges 22, 23 of the incontinence protector run together. The securing means consists of a two-part belt 28, 29, a first part 28 of the belt being arranged at one corner portion 24 on a first end edge 22 of the article, while a second part 29 of the belt is secured at the other corner portion 25 on the same end edge 22 of the article. The belt parts 28, 29 have fastening members 30 which are intended to cooperate with corresponding fastening members 31 arranged at the corner portions 26, 27 on the other end edge 23 of the incontinence protector. The cooperating fastening members can be hook-and-loop surfaces, adhesive surfaces, hooks, eyelets, snap fasteners, buttons and button holes, or the like. In addition, the fastening members 30 arranged on the belt 28, 29 can of course be designed to be secured to each other. In order to achieve a good fit of the incontinence protector, such fastening of the end portions of the belt 28, 29 can of course be combined with the belt also having securing members for securing to the backing layer 5.

Because the incontinence protector is carried on the user's body by way of the securing means 28, 29 arranged on the liquid barrier layer 3, the weight of the incontinence protector, and the tensile forces which occur in the securing means 28, 29, are essentially taken up by the liquid barrier layer 3. This means, for example, that the absorption body 1 remains virtually unaffected by these forces. Since, for example, fluff pulp, or other similar absorption material, has a relatively low tensile strength, undesired cracking, and thus an impaired absorption capacity, of the absorption body 1 is avoided.

Figure 2:
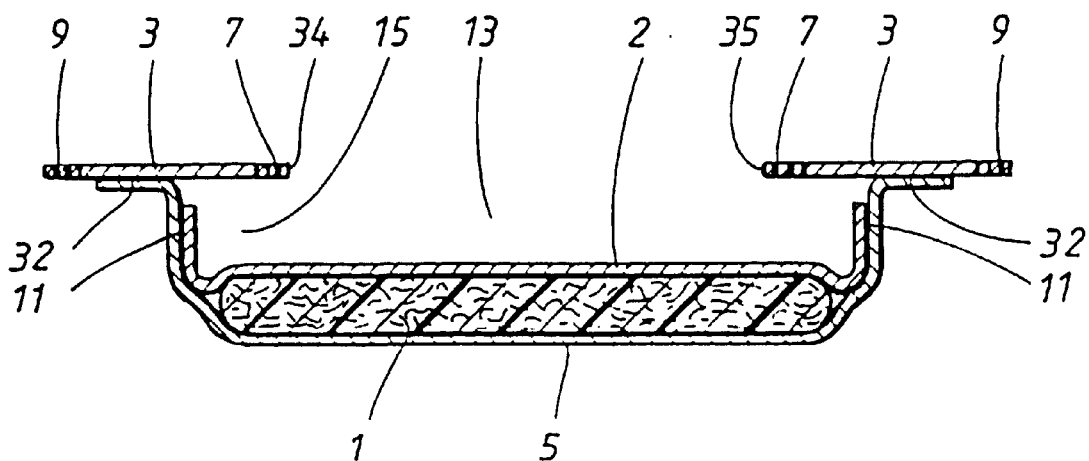
FIG. 2 shows a cross-section taken along the line A—A through the incontinence protector in FIG. 1.

In order to prevent soft faeces or sudden large flows of urine from causing leakages, the incontinence protector according to the invention is designed in such a way that the liquid-permeable surface layer 2 is secured to the inside of the liquid-impermeable backing layer 5, i.e. the surface of the liquid-impermeable backing layer 5 which is directed towards the absorption body 1. In addition, the liquid barrier layer 3 is also secured to the inside of the reverse layer 5. This is clearest in FIG. 2. This creates a space 15 or a pocket inside the liquid barrier layer 3, between this and the liquid-permeable surface layer 2, and also an edge portion of the liquid-impermeable backing layer 5. The space or pocket 15 is delimited by the edges 34, 35 of the opening 13 and by the seam 32 between the liquid barrier layer 3 and the backing layer 5 at the edge portion 11 of the incontinence protector.

Figure 3:
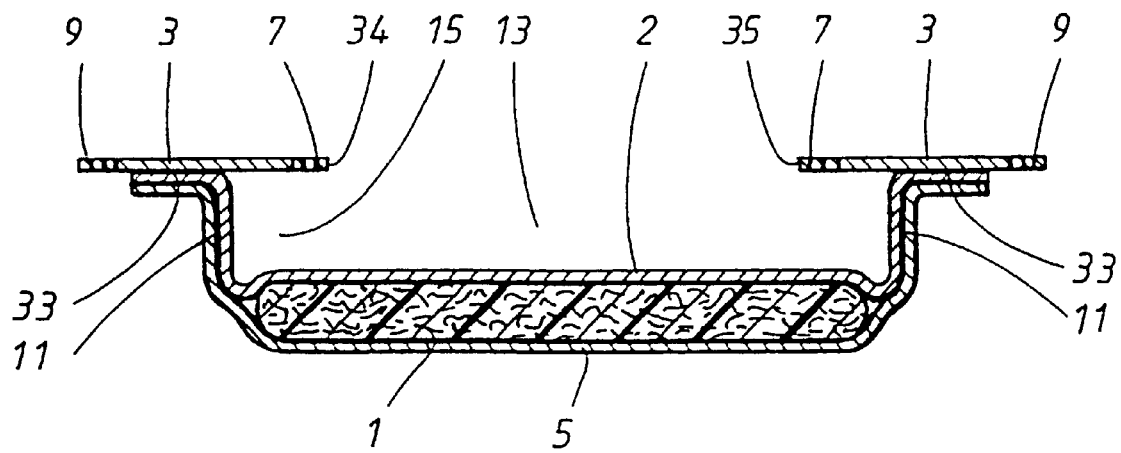
FIG. 3 shows an alternative design of the cross-section in FIG. 2.

It is also conceivable for the space 15 to be produced by means of the liquid-permeable surface layer 2 being at least partially secured to the inside of the liquid barrier layer 3. Such a design is shown in FIG. 3.

The space-15, delimited by the edges 34, 35 of the opening 13 and by the seam 33 arranged between the liquid-permeable surface layer 2 and the inside of the liquid barrier layer 3, is here found between the liquid-permeable surface layer 2 and the inside of the liquid barrier layer 3. The seam between the liquid barrier layer 3 and the liquid-permeable cover layer 2 extends down to the reverse layer 5. A liquid-impermeable seam is thus obtained between the liquid barrier layer 3 and the backing layer 5.

As has already been mentioned, all elastic which, during use, is expected to be affected by the movements of the user's body and body position is arranged in the material layer which, during use, is situated nearest the user's body, namely the liquid barrier layer 3. Such a positioning of the elastic members 7, 9 means that the elastic is already situated initially near the user's body. The elastic barriers which are formed by the elastic members and the liquid barrier layer therefore need only to be raised a little distance above the liquid-permeable surface layer 2 in order to achieve the desired sealing in respect of the user's body. This also minimizes the risk of material inadvertently getting between sealing surfaces and user, which situation can lead to both leakage and impaired comfort.

Another advantage is that the liquid barrier layer 3 is a relatively thin, flexible and conformable layer which is easily shaped by the elastic members and in this way can be made to adapt smoothly to the shape of the user's body.

In the illustrative embodiment shown, the incontinence protector is provided with two pairs of elastic members 7, 9. The first pair 7 is placed so that it essentially follows the edges 34, 35 of the opening 13, at least along the most part of the edges 34, 35 of the opening 13 which extend in the longitudinal direction of the incontinence protector. The elastic members 7 are secured to the liquid barrier layer 3 in the extended state. When the extension of the elastic members 7 ceases, the material in the liquid barrier layer 3 is drawn together so that the edges of the opening 13 are lifted up from the liquid-permeable surface layer 2. This creates a sealing effect between the raised edges around the opening 13 and the user's skin. This further ensures that body fluid passes directly from the user's genitals to the inner parts of the incontinence protector, as a result of which the risk of leakage of body fluid from between the edges 34, 35 of the opening 13 and the user's skin is minimal.

Prestressed elastic members can alternatively be obtained using material which is drawn together and becomes elastic only after heating. In this case, of course, the elastic members do not need to be secured to the barrier layer in the extended state in order to achieve the desired elastic effect.

Moreover, the incontinence protector in the illustrative embodiment is provided with a second pair of elastic members 9 which have the purpose of at least partially surrounding the user's legs during use. This second pair of elastic members 9 essentially follows the two side edges 20, 21 of the article, at least along most of the central parts of each respective side edge 20, 21.

In order to improve the function of the incontinence protector, the first pair of elastic members 7 is placed at a certain distance from the edge seam 32; 33 between the liquid barrier layer 3 and the liquid-permeable surface layer 2, or the backing layer 5. This facilitates the formation of the space 15 inside the liquid barrier layer 3. This space 15 is, as has previously been mentioned, of particular importance for securing against leakage when the user is lying on his/her side.

As can be seen in FIG. 1, the distance between an elastic member in the first pair of elastic members 7 and the corresponding elastic member in the second pair of elastic members 9 is smallest in the area of the article which, when used, is intended to be arranged in the user's groin area, in order then to diverge both forwards and backwards in the longitudinal direction of the article. The desired barriers are thus obtained at the same time as the shape of the elastic members 7, 9 gives the barrier layer a good anatomical fit, with consequently good comfort for the wearer. As has already been mentioned, supporting portions are to be understood as meaning those portions in which the incontinence protector is suspended on the user during use. These portions take up most of the tensile forces to which the incontinence protector is subjected during use and transmit the forces into the liquid barrier layer 3. Moreover, the shape of the opening 13 and the curvature of the two pairs of elastic members 7, 9 mean that the risk of the liquid barrier layer 3 blocking the inflow of liquid to the absorption body 1 during use is virtually nonexistent. Because the distance between the edges 34, 35 of the opening 13 and the respective side edges of the article 20, 21 is smallest in that area of the incontinence protector which chiefly risks. being squeezed together during use, only a small amount of liquid-barrier material is present in this area. There is thus very little risk that the narrow portions of the liquid barrier layer 3, on both sides of the opening 13 in the central part of the incontinence protector, will prevent liquid from reaching the absorption body 1. However, the shape of the opening 13 and the fact that the distance between the elastic members 7, 9 on both sides of the opening increases in the direction towards the end edges 22, 23 of the incontinence protector mean that liquid-absorbing, leakage-preventing pockets 15 are formed between the liquid barrier layer 3 and the liquid-permeable surface layer 2 at the end portions of the incontinence protector.

Since, in addition, the means for securing the incontinence protector on the user, i.e. the two parts 28, 29 of the securing belt, are supported by the corner portions 24–27 of the liquid barrier layer 3, the liquid barrier layer 3 thus constitutes the only directly force-absorbing layer in the incontinence protector. The use of a belt, which of course can be removable instead of being an integral part, as in the example shown, also permits a greater possibility of adjusting the fit of the incontinence protector, on the one hand by varying the is tensile force, and on the other hand by slightly altering the direction of tensioning. The latter is done by providing alternative fastening points for the strap parts 28, 29.

The invention must not be considered as being limited to the above-mentioned illustrative embodiment, as it can of course be applied in different embodiments within the context of the patent claims of the invention.

What is claimed is:

1. An absorbent article extending in a longitudinal direction, and comprising:

an inner surface, which in use, is intended to be directed towards a user;

an outer surface, which in use, is intended to be directed away from the user;

an elongate absorption body comprising at least one layer of absorbent material;

a liquid-impermeable backing layer at the outer surface;

a liquid-permeable surface layer at the inner surface;

said absorption body being enclosed between the backing layer and the liquid-permeable surface layer;

a first pair of elastic members extending in a direction which coincides with the longitudinal direction;

a second pair of elastic members extending in a direction which coincides with the longitudinal direction;

a liquid barrier layer arranged on the inner surface of the absorbent article with the liquid-permeable surface layer placed between the liquid impermeable backing layer and the liquid barrier layer;

the first pair of elastic members and the second pair of elastic members being secured solely and directly to the liquid barrier layer;

said liquid barrier layer being connected in a liquid-tight manner with a seam between the liquid barrier layer and the backing layer within an edge portion which includes said liquid barrier layer and said backing layer;

said edge portion running around the article;

said liquid barrier layer having an elongate opening which permits unimpeded passage of bodily excretions from genitals of the user to the liquid-permeable surface layer;

said backing layer being essentially nonelastic, whereby during use, the liquid barrier layer alone constitutes supporting portions of the article and all portions bearing against the user;

said liquid barrier layer having parts which are designed to directly or indirectly carry means for securing the article on the user; and one elastic member of said first pair of elastic members being separated from an adjacent elastic member of said second pair of elastic members by a distance which is smallest in an area of the article, which in use, is intended to be arranged at a groin of the user, and diverges forwards and backwards from said area in the longitudinal direction.

2. The absorbent article according to claim 1, further comprising a belt, which can be removed from the article, for securing the article on the user.

3. The absorbent article according to claim 1, further comprising a belt, which is an integral part of the article, for securing the article on the user.

4. The absorbent article according to claim 1, wherein the liquid-permeable surface layer is at least partially secured to an inner side of the liquid barrier layer; and a space, delimited by edges of the opening and the same between the liquid-permeable surface layer and the inside of the liquid barrier layer, is found between the liquid-permeable surface layer and the inner side of the liquid barrier layer.

5. The absorbent article according to claim 4, wherein the first pair of elastic members generally follows the edges of the opening, at least along a substantial part of the edges, which extend in the longitudinal direction of the article.

6. The absorbent article according to claim 1, wherein the liquid-permeable surface layer is secured to an inner side of the backing layer; and a space, delimited by edges of the opening and the seam arranged at the edge portion, is found between the liquid-permeable surface layer and an inner side of the liquid barrier layer.

7. The absorbent article according to claim 6, wherein the first pair of elastic members generally follows the edges of the opening, at least along a substantial part of the edges of the opening, which extend in the longitudinal direction of the article.

8. The absorbent article according to claim 7, wherein the second pair of elastic members principally follows two side edges of the article and extends at least along most of central parts of the respective side edge.

* * * * *